United States Patent
Ye et al.

(10) Patent No.: US 10,626,062 B2
(45) Date of Patent: *Apr. 21, 2020

(54) METHOD AND DEVICE FOR MANUFACTURING PROPENE AND C4 HYDROCARBON

(71) Applicant: DALIAN INSTITUTE OF CHEMICAL PHYSICS, CHINESE ACADEMY OF SCIENCES, Dalian (CN)

(72) Inventors: Mao Ye, Dalian (CN); Tao Zhang, Dalian (CN); Changqing He, Dalian (CN); Jinling Zhang, Dalian (CN); Xiangao Wang, Dalian (CN); Hailong Tang, Dalian (CN); Jinming Jia, Dalian (CN); Yinfeng Zhao, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/342,655

(22) PCT Filed: Oct. 19, 2016

(86) PCT No.: PCT/CN2016/102561
§ 371 (c)(1),
(2) Date: Apr. 17, 2019

(87) PCT Pub. No.: WO2018/072140
PCT Pub. Date: Apr. 26, 2018

(65) Prior Publication Data
US 2019/0241480 A1    Aug. 8, 2019

(51) Int. Cl.
C07C 1/22 (2006.01)
C07C 4/06 (2006.01)
(Continued)

(52) U.S. Cl.
CPC ............... *C07C 1/22* (2013.01); *B01J 8/00* (2013.01); *B01J 29/85* (2013.01); *B01J 38/30* (2013.01);
(Continued)

(58) Field of Classification Search
CPC .......... C07C 1/20; C07C 11/06; C07C 11/08; C07C 11/20; C07C 2529/85; C07C 4/06;
(Continued)

(56) References Cited

U.S. PATENT DOCUMENTS 5,914,433 A * 6/1999 Marker .................... B01J 29/84
208/49

FOREIGN PATENT DOCUMENTS

CN    101177374 A    5/2008
CN    101260013 A    9/2008
(Continued)

OTHER PUBLICATIONS

International Search Report dated Jul. 4, 2017 in corresponding International Application No. PCT/CN2016/102561; 4 pages.

*Primary Examiner* — Sharon Pregler
(74) *Attorney, Agent, or Firm* — Maier & Maier, PLLC (57) ABSTRACT

A method and device for preparing propylene and C4 hydrocarbons from oxygen-containing compounds. By circulating 80 wt. % or more of the hydrocarbons with five or more carbons in the product into a catalytic cracking lift pipe to perform a cracking reaction to generate a product containing propylene and C4 hydrocarbons, the method improves the reaction rate of ethylene alkylation, and the unit volume production capacity of reactor is high.

19 Claims, 1 Drawing Sheet

(51) Int. Cl.
*C07C 11/06* (2006.01)
*C07C 11/08* (2006.01)
*B01J 38/30* (2006.01)
*B01J 29/85* (2006.01)
*C07C 11/16* (2006.01)
*C07C 9/10* (2006.01)
*B01J 8/00* (2006.01)
*C07C 1/20* (2006.01)
*B01J 8/24* (2006.01)
*B01J 8/18* (2006.01)

(52) U.S. Cl.
CPC .................. *C07C 1/20* (2013.01); *C07C 4/06* (2013.01); *C07C 9/10* (2013.01); *C07C 11/06* (2013.01); *C07C 11/08* (2013.01); *C07C 11/16* (2013.01); *B01J 8/1872* (2013.01); *B01J 8/24* (2013.01); *C07C 2529/85* (2013.01); *Y02P 20/584* (2015.11); *Y02P 30/42* (2015.11)

(58) Field of Classification Search
CPC ... C07C 9/10; C07C 11/16; C07C 1/22; B01J 29/85; B01J 38/30; B01J 8/00; B01J 29/84; B01J 29/90; B01J 8/1872; B01J 8/24; B01J 8/388; B01D 45/12; Y02P 20/584; Y02P 20/52; Y02P 30/42
See application file for complete search history.

(56) References Cited

FOREIGN PATENT DOCUMENTS

| | | |
|---|---|---|
| CN | 101177374 B | 6/2011 |
| CN | 103804110 A | 5/2014 |
| CN | 104098429 A | 10/2014 |
| WO | 1999/18055 A1 | 4/1999 |
| WO | 2004/018089 A1 | 3/2004 |

* cited by examiner

METHOD AND DEVICE FOR MANUFACTURING PROPENE AND C4 HYDROCARBON

FIELD

The present invention refers to the field of chemical catalysis, in particular to a method and device for preparing propylene and C4 hydrocarbons from oxygen-containing compounds.

BACKGROUND

Propylene and butadiene are important chemical raw materials, which are usually obtained from naphtha cracking and steam cracking. The main sources of propylene are co-production of ethylene with propylene and by-product of refinery. The main source of butadiene is the further processing of C4 by-product produced in ethylene cracking process. In recent years, the technologies of methanol to olefin (MTO), methanol to propylene (MTP), ethane dehydrogenation to ethylene and propane dehydrogenation to propylene have been rapidly developed. There is an obvious tendency of raw material lightening in global olefin production, which will lead to the shortage of C4 resources. Therefore, it is necessary to develop a process that can produce propylene and C4 olefins with a high selectivity to meet market demand.

The fixed-bed methanol-to-olefin technology (WO2004/018089) was developed by LURGI AG in Germany. The technology utilized a ZSM-5 molecular sieve catalyst from Sud-Chemie AG to carry out methanol-to-olefin reaction in a fixed-bed reactor. The selectivity of propylene was close to 70%, and the by-products were ethylene, liquefied petroleum gas and gasoline.

The DMTO technology developed by Dalian Institute of Chemical Physics used a SAPO molecular sieve as catalyst, a dense-phase circulating fluidized-bed reactor and a methanol aqueous solution as raw material. The yield of ethylene and propylene in the product was about 80%, and more than 10% of C4 hydrocarbons were yielded as by-products.

Patent CN104098429A discloses a method of preparing propylene and C4 hydrocarbons from methanol in a circulating fluidized-bed using a ZSM-5 catalyst. The process features are that the raw material methanol and most of C1, C2 and C5 hydrocarbons in the product are entered into the circulating fluidized-bed reactor together, and propylene, C4 hydrocarbons, hydrocarbons of C6 and above and by-products are retrieved as final products.

Patent CN101177374B discloses a method for preparing olefins from methanol or dimethyl ether. The method includes the conversion of methanol or dimethyl ether, the alkylation of ethylene and methanol, and the catalytic cracking of components heavier than C4. Catalyst 1 is used for the methanol or dimethyl ether conversion and the ethylene and methanol alkylation in one reactor, and catalyst 2 is used for the catalytic cracking of components heavier than C4 in another reactor.

The methods disclosed in patents CN104098429A and CN101177374B share a common feature, that is, the selectivity of target products (propylene and C4) is increased through the recycling of light fractions (hydrocarbons with a carbon number of no more than 2). The alkylation of ethylene with methanol is the main reaction in the recycling reaction of the light fractions mentioned above.

The acidic molecular sieve catalysts can be used in both MTO reaction and alkylation of olefins. However, the rate of the MTO reaction is much higher than that of the alkylation of olefins. We have found that a fresh SAPO catalyst has a high activity, which is more beneficial to the alkylation of olefins. After a carbon deposition of catalyst, the reaction rate of alkylation of olefins will decrease rapidly.

Methanol is not only the raw material for the alkylation of olefins, but also the raw material for the MTO reaction. Therefore, the alkylation of olefins is necessarily accompanied by the MTO reaction. The MTO reaction will lead to a carbon deposition and lower activity of catalyst, which will hence inhibit the alkylation of olefins. An increase in the alkylation rate of olefins can reduce the content of light fractions in the product gas, and thus the unit volume production capacity of the reactor can be increased.

The methods disclosed in patents CN104098429A and CN101177374B do not refer to the reactor structure, nor do they clarify the flow modes of catalyst and raw material and the raw material distribution in the reactor. The method disclosed in patent CN101177374B uses a SAPO catalyst. The examples show that the mass ratio of methanol to light fractions is 1:10-20. Thus, it can be seen that the content of light fractions is very high and the unit volume production capacity of reactor is very low. A ZSM-5 catalyst is used in the method disclosed in patent CN104098429A. The content of hydrocarbons of C6 and above in the product is relatively high. The content of light fractions in the product gas is not disclosed in this method.

The preparation of propylene and C4 hydrocarbons with methanol and/or dimethyl ether as raw materials would necessarily lead to the simultaneous production of a certain amount of hydrocarbons with 5 or more carbons. The hydrocarbons with 5 or more carbons have a lower economic value, and can be converted through catalytic cracking into ethylene, propylene, C4 hydrocarbons, and the like, so as to increase the selectivity of propylene and C4 hydrocarbons.

From the above analysis, it can be seen that the main reactions for the preparation of propylene and C4 hydrocarbons from methanol are the MTO reaction and the alkylation of olefins. Therefore, the key to improve the selectivity of propylene and C4 hydrocarbons lies in a catalyst design and a reactor design. Avoiding the inhibition of the MTO reaction to the alkylation of olefins through an optimization in the reactor design is one of the important methods to improve the economics of methanol to propylene and C4 hydrocarbons.

SUMMARY

In view of the problem of low reaction rate of ethylene alkylation, the present invention provides a new method and device for increasing the reaction rate of ethylene alkylation in the process of preparing propylene and C4 hydrocarbons from methanol. Being used in the production of propylene and C4 hydrocarbons from oxygen-containing compounds, the method has the advantages of high yield of propylene and C4 hydrocarbons and good process economics.

To achieve the above purposes, one aspect of the present invention provides a device for preparing propylene and C4 hydrocarbons from oxygen-containing compounds, comprising:

a) a turbulent fluidized-bed reactor (1), the turbulent fluidized-bed reactor (1) comprises a reactor shell (2), n reactor feed distributors (3-1~3-n), a reactor gas-solid separator 1 (4), a reactor gas-solid separator 2 (5), a reactor heat extractor (6), a product gas outlet (7) and a reactor stripper (8), wherein the lower part of the turbulent fluidized-bed reactor (1) is a reaction zone, the upper part of the turbulent fluidized-bed reactor (1) is a settling zone, the n reactor feed distributors (3-1~3-n) are disposed in the reaction zone (preferably, the n reactor feed distributors are disposed in the reaction zone from bottom to top, and 0<n<10), the reactor heat extractor (6) is disposed in the reaction zone, the reactor gas-solid separator 1 (4) and the reactor gas-solid separator 2 (5) are placed in the settling zone or outside the reactor shell (2), the inlet of the reactor gas-solid separator 1 (4) is connected to a regenerated catalyst lift pipe (24), the catalyst outlet of the reactor gas-solid separator 1 (4) is located at the bottom of the reaction zone, the gas outlet of the reactor gas-solid separator 1 (4) is located in the settling zone, the inlet of the reactor gas-solid separator 2 (5) is located in the settling zone, the catalyst outlet of the reactor gas-solid separator 2 (5) is placed in the reaction zone, the gas outlet of the reactor gas-solid separator 2 (5) is connected to the product gas outlet (7), and the reactor stripper (8) passes through the reactor shell (2) from outside to inside at the bottom of the turbulent fluidized-bed reactor (1) and is opened in the reaction zone of the turbulent fluidized-bed reactor (1) (preferably, the horizontal height of opening of the reactor stripper in the reactor shell is higher than 1/10 the height of the reaction zone);

b) a catalytic cracking lift pipe (28), the bottom of the catalytic cracking lift pipe (28) is connected to the outlet of a catalytic cracking inclined pipe (26) and is provided with an inlet of hydrocarbons with 5 or more carbons (29), and the outlet of the catalytic cracking lift pipe (28) is connected to the settling zone of the turbulent fluidized-bed reactor (1);

c) a fluidized-bed regenerator (14), the fluidized-bed regenerator (14) comprises a regenerator shell (15), a regenerator feed distributor (16), a regenerator gas-solid separator (17), a regenerator heat extractor (18), a flue gas outlet (19) and a regenerator stripper (20), wherein the lower part of the fluidized-bed regenerator (14) is a regeneration zone, the upper part of the fluidized-bed regenerator (14) is a settling zone, the regenerator feed distributor (16) is placed at the bottom of the regeneration zone, the regenerator heat extractor (18) is placed in the regeneration zone, the regenerator gas-solid separator (17) is placed in the settling zone or outside the regenerator shell (15), the inlet of the regenerator gas-solid separator (17) is disposed in the settling zone, the catalyst outlet of the regenerator gas-solid separator (17) is disposed in the regeneration zone, the gas outlet of the regenerator gas-solid separator (17) is connected to the flue gas outlet (19), and the regenerator stripper (20) is opened at the bottom of the regenerator shell (15);

d) the bottom of the reactor stripper (8) is provided with a reactor stripping gas inlet (9), the bottom of the reactor stripper (8) is connected to the inlet of a inclined spent catalyst pipe (10), a spent catalyst sliding valve (11) is arranged in the inclined spent catalyst pipe (10), the outlet of the inclined spent catalyst pipe (10) is connected to the inlet of a spent catalyst lift pipe (12), the bottom of the spent catalyst lift pipe (12) is provided with a spent catalyst lifting gas inlet (13), and the outlet of the spent catalyst lift pipe (12) is connected to the settling section of the fluidized-bed regenerator (14);

e) the bottom of the regenerator stripper (20) is provided with a regenerator stripping gas inlet (21), the bottom of the regenerator stripper (20) is connected to the inlet of a inclined regenerated catalyst pipe (22), a regenerated catalyst sliding valve (23) is arranged in the inclined regenerated catalyst pipe (22), the outlet of the inclined regenerated catalyst pipe (22) is connected to the inlet of the regenerated catalyst lift pipe (24), the bottom of the regenerated catalyst lift pipe (24) is provided with a regenerated catalyst lifting gas inlet (25), and the outlet of the regenerated catalyst lift pipe (24) is connected to the inlet of the reactor gas-solid separator 1 (4);

the bottom of the regenerator stripper (20) is further connected to the inlet of the catalytic cracking inclined pipe (26), and a catalytic cracking sliding valve (27) is arranged in the catalytic cracking inclined pipe.

Another aspect of the present invention provides a method for preparing propylene and C4 hydrocarbons from oxygen-containing compounds, including:

a) feeding a raw material containing an oxygen-containing compound from n reactor feed distributors (3-1~3-n) to a reaction zone of a turbulent fluidized-bed reactor (1), and contacting the raw material with a catalyst, to generate a stream containing propylene and C4 hydrocarbons product and a spent catalyst containing carbon;

b) regenerating the spent catalyst by a fluidized-bed regenerator (14) to form a regenerated catalyst, wherein a part of the regenerated catalyst is fed to the bottom of the reaction zone of the turbulent fluidized-bed reactor (1) after being gas-solid separated by a reactor gas-solid separator 1 (4), and another part of the regenerated catalyst is fed to a catalytic cracking lift pipe (28) via a catalytic cracking inclined pipe (26);

c) sending the stream discharged from the turbulent fluidized-bed reactor (1) containing propylene and C4 hydrocarbons product into a product separation system, obtaining propylene, C4 hydrocarbons, light fractions, propane and hydrocarbons with 5 or more carbons after separation, wherein the light fractions contain more than 90 wt % of ethylene and a small amount of methane, ethane, hydrogen, CO and $CO_2$, returning 70 wt. % or more of the light fractions to the reaction zone of the turbulent fluidized-bed reactor (1) from the reactor feed distributor (3-1) at the bottom-most of the turbulent fluidized-bed reactor (1) to react ethylene and the oxygen-containing compounds to perform an alkylation reaction in presence of the catalyst to produce a product containing propylene, and retrieving less than 30 wt. % of the light fractions as a by-product;

d) feeding 80 wt. % or more of the hydrocarbons with 5 or more carbons coming from the separation system into the catalytic cracking lift pipe (28) via an inlet of hydrocarbons with 5 or more carbons (29), to contact cocurrent with the regenerated catalyst coming from the catalytic cracking inclined pipe (26) to perform a cracking reaction to generate a stream containing propylene and C4 hydrocarbons and a carbon-containing catalyst, subsequently, feeding the stream containing propylene and C4 hydrocarbons and the carbon-containing catalyst into a settling zone of the turbulent fluidized-bed reactor (1) via the outlet of the catalytic cracking lift pipe (28), and retrieving less than 20 wt. % of the hydrocarbons with 5 or more carbons as a by-product.

Preferably, the method in the present invention is carried out using the device for preparing propylene and C4 hydrocarbons from oxygen-containing compounds according to the first aspect, wherein the spent catalyst passes through the reactor stripper (8), the inclined spent catalyst pipe (10), the spent catalyst sliding valve (11) and the spent catalyst lift pipe (12) into the settling section of the fluidized-bed regenerator (14);

a regeneration medium enters the regeneration zone of the fluidized-bed regenerator (14) from the regenerator feed distributor (16), the regeneration medium reacts with the spent catalyst to perform calcination to produce a flue gas containing CO and $CO_2$ and the regenerated catalyst, and the flue gas is discharged after dust removal by the regenerator gas-solid separator (17);

a part of the regenerated catalyst passes through the regenerator stripper (20), the inclined regenerated catalyst pipe (22), the regenerated catalyst sliding valve (23) and the regenerated catalyst lift pipe (24) into the inlet of the reactor gas-solid separator 1 (4), and enters the bottom of the reaction zone of the turbulent fluidized-bed reactor (1) after gas-solid separation; another part of the regenerated catalyst passes through the regenerator stripper (20), the catalytic cracking inclined pipe (26) and the catalytic cracking sliding valve (27) into the catalytic cracking lift pipe (28);

a reactor stripping gas enters the reactor stripper (8) via the reactor stripping gas inlet (9) and contacts countercurrent with the spent catalyst, and then enters the turbulent fluidized-bed reactor (1); a spent catalyst lifting gas enters the spent catalyst lift pipe (12) via the spent catalyst lifting gas inlet (13) and contacts cocurrent with the spent catalyst, and then enters the settling section of the fluidized-bed regenerator (14);

a regenerator stripping gas enters the regenerator stripper (20) via the regenerator stripping gas inlet (21) and contacts countercurrent with the regenerated catalyst, and then enters the fluidized-bed regenerator (14); a regenerated catalyst lifting gas enters the regenerated catalyst lift pipe (24) via the regenerated catalyst lifting gas inlet (25) and contacts cocurrent with the regenerated catalyst, and then enters the inlet of the reactor gas-solid separator 1 (4).

The main characteristics of the turbulent fluidized-bed reactor in the present invention are that the light fractions enter from the reactor feed distributor at the bottom-most, the oxygen-containing compound enters from n reactor feed distributors respectively, and the regenerated catalyst directly enters the bottom of the reaction zone. On one hand, in the lower part of the reaction zone, the catalyst has a high activity, which is advantageous to the alkylation of ethylene, propylene and methanol; on the other hand, because of the multi-stage feeding of the oxygen-containing compounds, the case where most of the conversion reactions of the oxygen-containing compounds are completed in a small region of the lower part of the reaction zone is avoided, so that the concentration of the oxygen-containing compounds is more uniform in most of the reaction zone, weakening the inhibition of MTO reaction to the alkylation of olefins. Therefore, the turbulent fluidized-bed reactor in the present invention can effectively improve the alkylation reaction rate of olefins, and the unit volume production capacity of the reactor is high.

The main characteristics of the catalytic cracking lift pipe in the present invention are that the outlet of the catalytic cracking lift pipe is connected directly to the settling zone of the turbulent fluidized-bed reactor, and the catalytic cracking lift pipe and the turbulent fluidized-bed reactor share the gas-solid separator 2.

Preferably, the fluidized-bed regenerator in the present invention is a turbulent fluidized-bed regenerator.

Preferably, the reactor gas-solid separator 1, the reactor gas-solid separator 2 and the regenerator gas-solid separator in the present invention are cyclone separators.

In the method of the present invention, the MTO reaction produces ethylene, propylene, and the like, and the alkylation of olefins consumes ethylene, propylene, and the like. Since the reaction rate of ethylene alkylation is high, the content of light fractions in the product gas is low, and the circulating amount of the light fractions is low. In the method of the present invention, the circulating amount of the light fractions is 5-40 wt. % of the feeding amount of the oxygen-containing compound.

In the method of the present invention, the hydrocarbons with 5 or more carbons are circulated in the system, and the circulating amount of the hydrocarbons with 5 or more carbons is 2-20 wt. % of the feeding amount of the oxygen-containing compound.

In the method of the present invention, 70 wt. % or more of the light fractions and 80 wt. % or more of the hydrocarbons with 5 or more carbons are circulated in the system, and the release rate of the light fractions and the hydrocarbons with 5 or more carbons affects the composition of the product gas in the equilibrium state. In the equilibrium state, the product gas consists of 20-50 wt. % propylene, 15-40 wt. % C4 hydrocarbons, 10-45 wt. % light fractions, 0-5 wt. % propane and 5-20 wt. % hydrocarbons with 5 or more carbons. The light fractions contain more than 90 wt %, e.g. >95 wt. % ethylene, and other components include methane, ethane, hydrogen, CO and $CO_2$.

In a preferred embodiment, the catalyst contains a SAPO molecular sieve, and the catalyst simultaneously has the functions of methanol to olefins, alkylation of olefins and catalytic cracking.

In a preferred embodiment, the carbon content of the regenerated catalyst is less than 2 wt. %, and further preferably, the carbon content of the regenerated catalyst is less than 0.5 wt. %.

In a preferred embodiment, the carbon content of the spent catalyst is 5-12 wt. %, and further preferably, the carbon content of the spent catalyst is 5-10 wt. %.

In a preferred embodiment, the reaction conditions in the reaction zone of the turbulent fluidized-bed reactor (1) are as follows: the apparent linear velocity of gas is in a range from 0.1 m/s to 2 m/s, the reaction temperature is in a range from 300° C. to 550° C., the reaction pressure is in a range from 100 kPa to 500 kPa, and the bed density is in a range from 200 $kg/m^3$ to 1200 $kg/m^3$.

In a preferred embodiment, the reaction conditions in the catalytic cracking lift pipe (28) are as follows: the apparent linear velocity of gas is in a range from 2.0 m/s to 10.0 m/s, the reaction temperature is in a range from 400° C. to 750° C., the reaction pressure is in a range from 100 kPa to 500 kPa, and the bed density is in a range from 30 $kg/m^3$ to 300 $kg/m^3$.

In a preferred embodiment, the reaction conditions in the regeneration zone of the fluidized-bed regenerator (14) are as follows: the apparent linear velocity of gas is in a range from 0.1 m/s to 2 m/s, the regeneration temperature is in a range from 500° C. to 750° C., the regeneration pressure is in a range from 100 kPa to 500 kPa, and the bed density is in a range from 200 $kg/m^3$ to 1200 $kg/m^3$.

In a preferred embodiment, the oxygen-containing compound is methanol and/or dimethyl ether; and/or the regeneration medium is any one of air, oxygen-poor air or water vapor or a mixture thereof; and/or the reactor stripping gas, the regenerator stripping gas, the spent catalyst lifting gas and the regenerated catalyst lifting gas are water vapor or nitrogen.

BRIEF DESCRIPTION OF THE FIGURES

The reference numerals in the FIGURE are listed as follows.

1—turbulent fluidized-bed reactor; 2—reactor shell; 3—reactor feed distributors (3-1~3-n); 4—reactor gas-solid separator 1; 5—reactor gas-solid separator 2; 6—reactor heat extractor; 7—product gas outlet; 8—reactor stripper; 9—reactor stripping gas inlet; 10—inclined spent catalyst pipe; 11—spent catalyst sliding valve; 12—spent catalyst lift pipe; 13—spent catalyst lifting gas inlet; 14—fluidized-bed regenerator; 15—regenerator shell; 16—regenerator feed distributor; 17—regenerator gas-solid separator; 18—regenerator heat extractor; 19—flue gas outlet; 20—regenerator stripper; 21—regenerator stripping gas inlet; 22—inclined regenerated catalyst pipe; 23—regenerated catalyst sliding valve; 24—regenerated catalyst lift pipe; 25—regenerated catalyst lifting gas inlet; 26—catalytic cracking inclined pipe; 27—catalytic cracking sliding valve; 28—catalytic cracking lift pipe; 29—inlet of hydrocarbons with 5 or more carbons.

DETAILED DESCRIPTION

Figure 1:
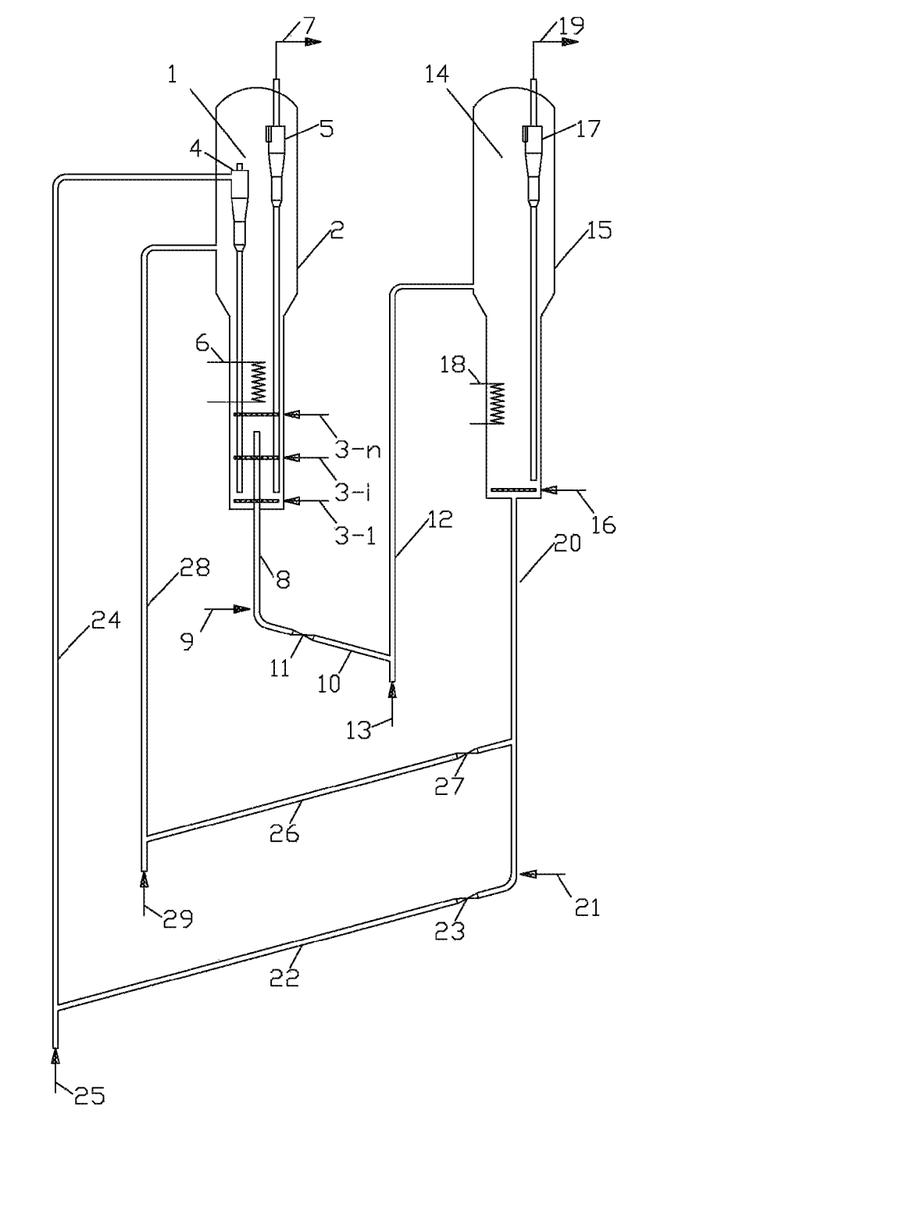
FIG. 1 is a schematic diagram of a device for preparing propylene and C4 hydrocarbons from oxygen-containing compounds according to an embodiment of the present invention.

In a specific embodiment, the schematic diagram of the device according to the present invention for preparing propylene and C4 hydrocarbons from oxygen-containing compounds is shown in FIG. 1, which comprises:

a) a turbulent fluidized-bed reactor (1), the turbulent fluidized-bed reactor (1) comprises a reactor shell (2), n reactor feed distributors (3-1~3-n), a reactor gas-solid separator 1 (4), a reactor gas-solid separator 2 (5), a reactor heat extractor (6), a product gas outlet (7) and a reactor stripper (8), wherein the lower part of the turbulent fluidized-bed reactor (1) is a reaction zone, the upper part of the turbulent fluidized-bed reactor (1) is a settling zone, the n reactor feed distributors (3-1~3-n) are disposed in the reaction zone from bottom to top and 0<n<10, the reactor heat extractor (6) is disposed in the reaction zone, the reactor gas-solid separator 1 (4) and the reactor gas-solid separator 2 (5) are placed in the settling zone or outside the reactor shell (2), the inlet of the reactor gas-solid separator 1 (4) is connected to a regenerated catalyst lift pipe (24), the catalyst outlet of the reactor gas-solid separator 1 (4) is located at the bottom of the reaction zone, the gas outlet of the reactor gas-solid separator 1 (4) is located in the settling zone, the inlet of the reactor gas-solid separator 2 (5) is located in the settling zone, the catalyst outlet of the reactor gas-solid separator 2 (5) is placed in the reaction zone, the gas outlet of the reactor gas-solid separator 2 (5) is connected to the product gas outlet (7), and the inlet of the reactor stripper (8) is in the reaction zone of the turbulent fluidized-bed reactor (1), with the horizontal height higher than $1/10$ that of the reaction zone;

b) a catalytic cracking lift pipe (28), the bottom of the catalytic cracking lift pipe (28) is provided with an inlet of hydrocarbons with 5 or more carbons (29), the outlet of the catalytic cracking lift pipe (28) is connected to the settling zone of the turbulent fluidized-bed reactor (1), the inlet of the catalytic cracking lift pipe (28) is connected to the outlet of a catalytic cracking inclined pipe (26), a catalytic cracking sliding valve (27) is arranged in the catalytic cracking inclined pipe (26), and the inlet of the catalytic cracking inclined pipe (26) is connected to a regenerator stripper (20);

c) a fluidized-bed regenerator (14), the fluidized-bed regenerator (14) comprises a regenerator shell (15), a regenerator feed distributor (16), a regenerator gas-solid separator (17), a regenerator heat extractor (18), a flue gas outlet (19) and the regenerator stripper (20), wherein the lower part of the fluidized-bed regenerator (14) is a regeneration zone, the upper part of the fluidized-bed regenerator (14) is a settling zone, the regenerator feed distributor (16) is placed at the bottom of the regeneration zone, the regenerator heat extractor (18) is placed in the regeneration zone, the regenerator gas-solid separator (17) is placed in the settling zone or outside the regenerator shell (15), the inlet of the regenerator gas-solid separator (17) is disposed in the settling zone, the catalyst outlet of the regenerator gas-solid separator (17) is disposed in the regeneration zone, the gas outlet of the regenerator gas-solid separator (17) is connected to the flue gas outlet (19), and the inlet of the regenerator stripper (20) is connected to the bottom of the regenerator shell (15);

d) the bottom of the reactor stripper (8) is provided with a reactor stripping gas inlet (9), the bottom of the reactor stripper (8) is connected to the inlet of a inclined spent catalyst pipe (10), a spent catalyst sliding valve (11) is arranged in the inclined spent catalyst pipe (10), the outlet of the inclined spent catalyst pipe (10) is connected to the inlet of a spent catalyst lift pipe (12), the bottom of the spent catalyst lift pipe (12) is provided with a spent catalyst lifting gas inlet (13), and the outlet of the spent catalyst lift pipe (12) is connected to the settling section of the fluidized-bed regenerator (14);

e) the bottom of the regenerator stripper (20) is provided with a regenerator stripping gas inlet (21), the bottom of the regenerator stripper (20) is connected to the inlet of a inclined regenerated catalyst pipe (22), a regenerated catalyst sliding valve (23) is arranged in the inclined regenerated catalyst pipe (22), the outlet of the inclined regenerated catalyst pipe (22) is connected to the inlet of the regenerated catalyst lift pipe (24), the bottom of the regenerated catalyst lift pipe (24) is provided with a regenerated catalyst lifting gas inlet (25), and the outlet of the regenerated catalyst lift pipe (24) is connected to the inlet of the reactor gas-solid separator 1 (4).

In the above embodiment, the fluidized-bed regenerator (14) may be a turbulent fluidized-bed regenerator; the reactor gas-solid separator 1 (4), the reactor gas-solid separator 2 (5) and the regenerator gas-solid separator (17) may be cyclone separators.

In a specific embodiment, the method according to the present invention for preparing propylene and C4 hydrocarbons from oxygen-containing compounds includes the following steps:

a) feeding a raw material containing oxygen-containing compounds from the n reactor feed distributors (3-1~3-n) to the reaction zone of the turbulent fluidized-bed reactor (1), and contacting the raw material with a catalyst, to generate a stream containing propylene and C4 hydrocarbons product and a spent catalyst containing carbon;

b) sending the stream discharged from the turbulent fluidized-bed reactor (1) containing propylene and C4 hydrocarbons product into the product separation system, obtaining propylene, C4 hydrocarbons, light fractions, propane and hydrocarbons with 5 or more carbons after separation, wherein the light fractions contain more than 90 wt % of ethylene and a small amount of methane, ethane, hydrogen, CO and $CO_2$, returning 70-98 wt. % of the light fractions to the reaction zone of the turbulent fluidized-bed reactor (1) from the reactor feed distributor (3-1) at the bottommost of the turbulent fluidized-bed reactor (1) to react ethylene and the oxygen-containing compounds to perform an alkylation reaction in presence of the catalyst to produce a product containing propylene, and retrieving less than 30 wt. % of the light fractions as a by-product;

c) feeding 80 wt. % or more of the hydrocarbons with 5 or more carbons coming from the separation system into the catalytic cracking lift pipe (28) via the inlet of hydrocarbons with 5 or more carbons (29), to contact cocurrent with the regenerated catalyst coming from the catalytic cracking inclined pipe (26) to perform a cracking reaction to generate a stream containing propylene and C4 hydrocarbons and a carbon-containing catalyst, subsequently, feeding the stream containing propylene and C4 hydrocarbons and the carbon-containing catalyst into the settling zone of the turbulent fluidized-bed reactor (1) via the outlet of the catalytic cracking lift pipe (28), and retrieving less than 20 wt. % of the hydrocarbons with 5 or more carbons as a by-product;

d) the spent catalyst passes through the reactor stripper (8), the inclined spent catalyst pipe (10), the spent catalyst sliding valve (11) and the spent catalyst lift pipe (12) into the settling section of the fluidized-bed regenerator (14);

e) a regeneration medium enters the regeneration zone of the fluidized-bed regenerator (14) from the regenerator feed distributor (16), the regeneration medium reacts with the spent catalyst to perform calcination to produce a flue gas containing CO and $CO_2$ and the regenerated catalyst, and the flue gas is discharged after dust removal by the regenerator gas-solid separator (17);

f) a part of the regenerated catalyst passes through the regenerator stripper (20), the inclined regenerated catalyst pipe (22), the regenerated catalyst sliding valve (23) and the regenerated catalyst lift pipe (24) into the inlet of the reactor gas-solid separator 1 (4), and enters the bottom of the reaction zone of the turbulent fluidized-bed reactor (1) after gas-solid separation; another part of the regenerated catalyst passes through the regenerator stripper (20), the catalytic cracking inclined pipe (26) and the catalytic cracking sliding valve (27) into the catalytic cracking lift pipe (28);

g) a reactor stripping gas enters the reactor stripper (8) via the reactor stripping gas inlet (9) and contacts countercurrent with the spent catalyst, and then enters the turbulent fluidized-bed reactor (1); a spent catalyst lifting gas enters the spent catalyst lift pipe (12) via the spent catalyst lifting gas inlet (13) and contacts cocurrent with the spent catalyst, and then enters the settling section of the fluidized-bed regenerator (14);

h) a regenerator stripping gas enters the regenerator stripper (20) via the regenerator stripping gas inlet (21) and contacts countercurrent with the regenerated catalyst, and then enters the fluidized-bed regenerator (14); a regenerated catalyst lifting gas enters the regenerated catalyst lift pipe (24) via the regenerated catalyst lifting gas inlet (25) and contacts cocurrent with the regenerated catalyst, and then enters the inlet of the reactor gas-solid separator 1 (4).

In order to better illustrate the present invention and facilitate the understanding of the technical scheme of the present invention, comparative examples and representative but non-restrictive examples of the present invention are listed as follows:

Example 1

The present example is a comparative example. The device shown in FIG. 1 is used, but the turbulent fluidized-bed reactor (1) does not contain the reactor gas-solid separator 1 (4), and the regenerated catalyst lift pipe (24) is directly connected to the settling zone of the turbulent fluidized-bed reactor (1).

The turbulent fluidized-bed reactor (1) contains three reactor feed distributors (3-1~3-3), the reactor gas-solid separator 1 (4) is placed outside the reactor shell (2), and the horizontal height of the inlet of the reactor stripper (8) is at ½ height of the reaction zone. The reaction conditions in the reaction zone of the turbulent fluidized-bed reactor (1) are as follows: the apparent linear velocity of gas is about 1.0 m/s, the reaction temperature is about 450° C., the reaction pressure is about 150 kPa, and the bed density is about 350 kg/m$^3$.

The reaction conditions in the catalytic cracking lift pipe (28) are as follows: the apparent linear velocity of gas is about 5.0 m/s, the reaction temperature is about 600° C., the reaction pressure is about 150 kPa, and the bed density is about 50 kg/m$^3$.

The reaction conditions in the regeneration zone of the fluidized-bed regenerator (14) are as follows: the apparent linear velocity of gas is about 1.0 m/s, the regeneration temperature is about 650° C., the regeneration pressure is about 150 kPa, and the bed density is about 350 kg/m$^3$.

The catalyst contains a SAPO molecular sieve. The carbon content of the spent catalyst is about 7%, and the carbon content of the regenerated catalyst is about 0.2 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 20 wt. % of the feeding amount of methanol, and 71 wt. % of the light fractions are circulated in the system. The circulating amount of the hydrocarbons with 5 or more carbons is 12 wt. % of the feeding amount of methanol, and 92 wt. % of the hydrocarbons with 5 or more carbons are circulated in the system.

The composition of the product gas discharged from the turbulent fluidized-bed reactor (1) is: 31 wt. % propylene, 19 wt. % C4 hydrocarbons, 29 wt. % light fractions, 2 wt. % propane and 19 wt. % hydrocarbons with 5 or more carbons. The light fractions contain 98 wt. % ethylene and 2 wt. % methane, ethane, hydrogen, CO, $CO_2$, and the like.

The composition of the product gas discharged from the separation system is: 50 wt. % propylene, 31 wt. % C4 hydrocarbons, 14 wt. % light fractions, 3 wt. % propane and 2 wt. % hydrocarbons with 5 or more carbons.

Example 2

The device shown in FIG. 1 is used. The turbulent fluidized-bed reactor (1) contains three reactor feed distributors (3-1~3-3), the reactor gas-solid separator 1 (4) is placed outside the reactor shell (2), and the horizontal height of the inlet of the reactor stripper (8) is at ½ height of the reaction zone. The reaction conditions in the reaction zone of the turbulent fluidized-bed reactor (1) are as follows: the apparent linear velocity of gas is about 1.0 m/s, the reaction temperature is about 450° C., the reaction pressure is about 150 kPa, and the bed density is about 350 kg/m³.

The reaction conditions in the catalytic cracking lift pipe (28) are as follows: the apparent linear velocity of gas is about 5.0 m/s, the reaction temperature is about 600° C., the reaction pressure is about 150 kPa, and the bed density is about 50 kg/m³.

The reaction conditions in the regeneration zone of the fluidized-bed regenerator (14) are as follows: the apparent linear velocity of gas is about 1.0 m/s, the regeneration temperature is about 650° C., the regeneration pressure is about 150 kPa, and the bed density is about 350 kg/m³.

The catalyst contains a SAPO molecular sieve. The carbon content of the spent catalyst is about 7%, and the carbon content of the regenerated catalyst is about 0.2 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 15 wt. % of the feeding amount of methanol, and 98 wt. % of the light fractions are circulated in the system. The circulating amount of the hydrocarbons with 5 or more carbons is 12 wt. % of the feeding amount of methanol, and 92 wt. % of the hydrocarbons with 5 or more carbons are circulated in the system.

The composition of the product gas discharged from the turbulent fluidized-bed reactor (1) is: 35 wt. % propylene, 23 wt. % C4 hydrocarbons, 21 wt. % light fractions, 2 wt. % propane and 19 wt. % hydrocarbons with 5 or more carbons. The light fractions contain 97 wt. % ethylene and 3 wt. % methane, ethane, hydrogen, CO, $CO_2$, and the like.

The composition of the product gas discharged from the separation system is: 57 wt. % propylene, 37 wt. % C4 hydrocarbons, 1 wt. % light fractions, 3 wt. % propane and 2 wt. % hydrocarbons with 5 or more carbons.

The present example is different from Example 1 (comparative example) merely in that the regenerated catalyst enters the bottom of the turbulent fluidized-bed reactor and contacts firstly with the light fractions, while in Example 1, the regenerated catalyst enters the settling zone of the turbulent fluidized-bed reactor. Comparing the present example with Example 1, it can be seen that the conversion rate of light fractions can be greatly improved when the catalyst is contacted firstly with the light fractions. The light fractions discharged from the separation system in present example is only 7% of that in the comparative example. Therefore, the device of the present invention effectively improves the reaction rate of ethylene alkylation.

Example 3

The present example is a comparative example. The device shown in FIG. 1 is used, but the catalytic cracking inclined pipe (26), the catalytic cracking sliding valve (27) and the catalytic cracking lift pipe (28) are not comprised. The hydrocarbons with 5 or more carbons are not recycled, but retrieved directly as a by-product.

The turbulent fluidized-bed reactor (1) contains four reactor feed distributors (3-1~3-4), the reactor gas-solid separator 1 (4) is placed in the settling zone, and the horizontal height of the inlet of the reactor stripper (8) is at ¾ height of the reaction zone. The reaction conditions in the reaction zone of the turbulent fluidized-bed reactor (1) are as follows: the apparent linear velocity of gas is about 1.2 m/s, the reaction temperature is about 360° C., the reaction pressure is about 200 kPa, and the bed density is about 300 kg/m³.

The reaction conditions in the regeneration zone of the fluidized-bed regenerator (14) are as follows: the apparent linear velocity of gas is about 1.2 m/s, the regeneration temperature is about 700° C., the regeneration pressure is about 200 kPa, and the bed density is about 300 kg/m³.

The catalyst contains a SAPO molecular sieve. The carbon content of the spent catalyst is about 8%, and the carbon content of the regenerated catalyst is about 0.1 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 16 wt. % of the feeding amount of methanol, and 90 wt. % of the light fractions are circulated in the system.

The composition of the product gas discharged from the turbulent fluidized-bed reactor (1) is: 39 wt. % propylene, 25 wt. % C4 hydrocarbons, 29 wt. % light fractions, 2 wt. % propane and 5 wt. % hydrocarbons with 5 or more carbons. The light fractions contain 96 wt. % ethylene and 4 wt. % methane, ethane, hydrogen, CO, $CO_2$, and the like.

The composition of the product gas discharged from the separation system is: 53 wt. % propylene, 33 wt. % C4 hydrocarbons, 4 wt. % light fractions, 3 wt. % propane and 7 wt. % hydrocarbons with 5 or more carbons.

Example 4

The device shown in FIG. 1 is used. The turbulent fluidized-bed reactor (1) contains four reactor feed distributors (3-1~3-4), the reactor gas-solid separator 1 (4) is placed in the settling zone, and the horizontal height of the inlet of the reactor stripper (8) is at ¾ height of the reaction zone. The reaction conditions in the reaction zone of the turbulent fluidized-bed reactor (1) are as follows: the apparent linear velocity of gas is about 1.2 m/s, the reaction temperature is about 360° C., the reaction pressure is about 200 kPa, and the bed density is about 300 kg/m³.

The reaction conditions in the catalytic cracking lift pipe (28) are as follows: the apparent linear velocity of gas is about 7.0 m/s, the reaction temperature is about 650° C., the reaction pressure is about 200 kPa, and the bed density is about 40 kg/m³.

The reaction conditions in the regeneration zone of the fluidized-bed regenerator (14) are as follows: the apparent linear velocity of gas is about 1.2 m/s, the regeneration temperature is about 700° C., the regeneration pressure is about 200 kPa, and the bed density is about 300 kg/m³.

The catalyst contains a SAPO molecular sieve. The carbon content of the spent catalyst is about 8%, and the carbon content of the regenerated catalyst is about 0.1 wt. %.

The oxygen-containing compound is methanol, and the regeneration medium is air; the reactor stripping gas, the regenerator stripping gas, the spent catalyst lifting gas and the regenerated catalyst lifting gas are water vapor.

The circulating amount of the light fractions is 16 wt. % of the feeding amount of methanol, and 90 wt. % of the light fractions are circulated in the system. The circulating amount of the hydrocarbons with 5 or more carbons is 4 wt. % of the feeding amount of methanol, and 95 wt. % of the hydrocarbons with 5 or more carbons are circulated in the system.

The composition of the product gas discharged from the turbulent fluidized-bed reactor (1) is: 34 wt. % propylene, 23 wt. % C4 hydrocarbons, 25 wt. % light fractions, 2 wt. % propane and 16 wt. % hydrocarbons with 5 or more carbons. The light fractions contain 96 wt. % ethylene and 4 wt. % methane, ethane, hydrogen, CO, $CO_2$, and the like.

The composition of the product gas discharged from the separation system is: 55 wt. % propylene, 37 wt. % C4 hydrocarbons, 4 wt. % light fractions, 3 wt. % propane and 1 wt. % hydrocarbons with 5 or more carbons.

The present example is different from Example 3 (comparative example) merely in that the hydrocarbons with 5 or more carbons are recycled. Comparing the present example with Example 3, it can be seen that the hydrocarbons with 5 or more carbons discharged from the separation system in present example is only 14% of that in the comparative example. Therefore, the device of the present invention can effectively convert the hydrocarbons with 5 or more carbons into propylene and C4 hydrocarbons through catalytic cracking.

Example 5

The device shown in FIG. 1 is used. The turbulent fluidized-bed reactor (1) contains six reactor feed distributors (3-1~3-6), the reactor gas-solid separator 1 (4) is placed in the settling zone, and the horizontal height of the inlet of the reactor stripper (8) is at ⅚ height of the reaction zone. The reaction conditions in the reaction zone of the turbulent fluidized-bed reactor (1) are as follows: the apparent linear velocity of gas is about 1.5 m/s, the reaction temperature is about 420° C., the reaction pressure is about 250 kPa, and the bed density is about 250 kg/m³.

The reaction conditions in the catalytic cracking lift pipe (28) are as follows: the apparent linear velocity of gas is about 7.0 m/s, the reaction temperature is about 700° C., the reaction pressure is about 250 kPa, and the bed density is about 40 kg/m³.

The reaction conditions in the regeneration zone of the fluidized-bed regenerator (14) are as follows: the apparent linear velocity of gas is about 1.5 m/s, the regeneration temperature is about 700° C., the regeneration pressure is about 250 kPa, and the bed density is about 250 kg/m³.

The catalyst contains a SAPO molecular sieve. The carbon content of the spent catalyst is about 9%, and the carbon content of the regenerated catalyst is about 0.05 wt. %.

The oxygen-containing compound is dimethyl ether, and the regeneration medium is oxygen-poor air; the reactor stripping gas, the regenerator stripping gas, the spent catalyst lifting gas and the regenerated catalyst lifting gas are nitrogen.

The circulating amount of the light fractions is 19 wt. % of the feeding amount of dimethyl ether, and 85 wt. % of the light fractions are circulated in the system. The circulating amount of the hydrocarbons with 5 or more carbons is 14 wt. % of the feeding amount of dimethyl ether, and 90 wt. % of the hydrocarbons with 5 or more carbons are circulated in the system.

The composition of the product gas discharged from the turbulent fluidized-bed reactor (1) is: 35 wt. % propylene, 23 wt. % C4 hydrocarbons, 23 wt. % light fractions, 3 wt. % propane and 16 wt. % hydrocarbons with 5 or more carbons. The light fractions contain 96 wt. % ethylene and 4 wt. % methane, ethane, hydrogen, CO, $CO_2$, and the like.

The composition of the product gas discharged from the separation system is: 53 wt. % propylene, 35 wt. % C4 hydrocarbons, 5 wt. % light fractions, 5 wt. % propane and 2 wt. % hydrocarbons with 5 or more carbons.

The present invention has been described in detain as above. However, the present invention is not limited to the specific embodiments as mentioned herein. It will be understood that without departing from the scope of the present invention, any slight variations and modifications may be made by those skilled in the art. The scope of the present invention is limited by the claims as appended.

The invention claimed is:

1. A device for preparing propylene and C4 hydrocarbons from oxygen-containing compounds, comprising:
   a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;
   a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and
   a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe.

2. The device according to claim 1, wherein the one or more reactor feed distributors are disposed in the reaction zone from bottom to top, and there are between 1 and 10 distributors.

3. The device according to claim 1, wherein the horizontal height of opening of the reactor stripper in the reactor shell is higher than 1/10 the height of the reaction zone.

4. The device according to claim 1, wherein the catalytic cracking lift pipe and the turbulent fluidized-bed reactor share the second gas-solid separator.

5. The device according to claim 1, wherein the fluidized-bed regenerator is a turbulent fluidized-bed regenerator.

6. The device according to claim 1, wherein the first reactor gas-solid separator, the second reactor gas-solid separator and the regenerator gas-solid separator are cyclone separators.

7. A method for preparing propylene and C4 hydrocarbons from oxygen-containing compounds, including:
feeding a raw material containing an oxygen-containing compound from one or more reactor feed distributors to a reaction zone of a turbulent fluidized-bed reactor, and contacting the raw material with a catalyst, to generate a stream containing propylene and C4 hydrocarbons product and a spent catalyst containing carbon;
regenerating the spent catalyst by a fluidized-bed regenerator to form a regenerated catalyst, wherein a part of the regenerated catalyst is fed to the bottom of the reaction zone of the turbulent fluidized-bed reactor after being gas-solid separated by a first reactor gas-solid separator NE and another part of the regenerated catalyst is fed to a catalytic cracking lift pipe via a catalytic cracking inclined pipe;

sending the stream discharged from the turbulent fluidized-bed reactor containing propylene and C4 hydrocarbons product into a product separation system, obtaining propylene, C4 hydrocarbons, light fractions, propane and hydrocarbons with 5 or more carbons after separation, wherein the light fractions contain more than 90 wt % of ethylene and a small amount of methane, ethane, hydrogen, CO and $CO_2$, returning 70 wt. % or more of the light fractions to the reaction zone of the turbulent fluidized-bed reactor from the reactor feed distributor at the bottom-most of the turbulent fluidized-bed reactor to react ethylene and the oxygen-containing compounds to perform an alkylation reaction in presence of the catalyst to produce a product containing propylene, and retrieving less than 30 wt. % of the light fractions as a by-product;

feeding 80 wt. % or more of the hydrocarbons with 5 or more carbons coming from the product separation system into the catalytic cracking lift pipe via a hydrocarbons with 5 or more carbons inlet, to contact cocurrent with the regenerated catalyst coming from the catalytic cracking inclined pipe to perform a cracking reaction to generate a stream containing propylene and C4 hydrocarbons and a carbon-containing catalyst, subsequently, feeding the stream containing propylene and C4 hydrocarbons and the carbon-containing catalyst into a settling zone of the turbulent fluidized-bed reactor via the outlet of the catalytic cracking lift pipe, and retrieving less than 20 wt. % of the hydrocarbons with 5 or more carbons as a by-product.

8. The method according to claim 7, being carried out by using a device, comprising:
a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;
a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

9. The method according to claim 7, wherein the catalyst contains a SAPO molecular sieve.

10. The method according to claim 7, wherein the circulating amount of the light fractions is 5-40 wt. % of the feeding amount of the oxygen-containing compound.

11. The method according to claim 7, wherein the circulating amount of the hydrocarbons with 5 or more carbons is 2-20 wt. % of the feeding amount of the oxygen-containing compound.

12. The method according to claim 7, wherein the carbon content of the spent catalyst is 5-12 wt. %, and the carbon content of the regenerated catalyst is less than 2 wt. %.

13. The method according to claim 7, wherein the oxygen-containing compound is methanol and/or dimethyl ether; and/or the regeneration medium is any one of air, oxygen-poor air or water vapor or a mixture thereof; and/or the reactor stripping gas, the regenerator stripping gas, the spend catalyst lifting gas and the regenerated catalyst lifting gas are water vapor or nitrogen.

14. The method according to claim 7, wherein the reaction conditions in the reaction zone of the turbulent fluidized-bed reactor are: the apparent linear velocity of gas is in a range from 0.1 m/s to 2 m/s, the reaction temperature is in a range from 300° C. to 550° C., the reaction pressure is in a range from 100 kPa to 500 kPa, and the bed density is in a range from 200 $kg/m^3$ to 1200 $kg/m^3$; and/or the reaction conditions in the catalytic cracking lift pipe are: the apparent linear velocity of gas is in a range from 2.0 m/s to 10.0 m/s, the reaction temperature is in a range from 400° C. to 750° C., the reaction pressure is in a range from 100 kPa to 500 kPa, and the bed density is in a range from 30 $kg/m^3$ to 300 $kg/m^3$; and/or the reaction conditions in the regeneration zone of the fluidized-bed regenerator are: the apparent linear velocity of gas is in a range from 0.1 m/s to 2 m/s, the regeneration temperature is in a range from 500° C. to 750° C., the regeneration pressure is in a range from 100 kPa to 500 kPa, and the bed density is in a range from 200 $kg/m^3$ to 1200 $kg/m^3$.

15. The method according to claim 7, being carried out by using a device, comprising:

a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;

a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe;

the one or more reactor feed distributors are disposed in the reaction zone from bottom to top, and there are between 1 and 10 distributors; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

16. The method according to claim 7, being carried out by using a device, comprising:

a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;

a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe;

the horizontal height of opening of the reactor stripper in the reactor shell is higher than $\frac{1}{10}$ the height of the reaction zone; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

17. The method according to claim 7, being carried out by using a device, comprising:

a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;

a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe;

the catalytic cracking lift pipe and the turbulent fluidized-bed reactor share the second gas-solid separator; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

18. The method according to claim 7, being carried out by using a device, comprising:

a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;

a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe;

the fluidized-bed regenerator is a turbulent fluidized-bed regenerator; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

19. The method according to claim 7, being carried out by using a device, comprising:

a turbulent fluidized-bed reactor, the turbulent fluidized-bed reactor comprises a reactor shell, one or more reactor feed distributors, a first reactor gas-solid separator, a second reactor gas-solid separator, a reactor heat extractor, a product gas outlet and a reactor stripper, wherein the lower part of the turbulent fluidized-bed reactor is a reaction zone, the upper part of the turbulent fluidized-bed reactor is a settling zone, the one or more reactor feed distributors are disposed in the reaction zone, the reactor heat extractor is disposed in the reaction zone, the first reactor gas-solid separator and the second reactor gas-solid separator are placed in the settling zone or outside the reactor shell, the inlet of the first reactor gas-solid separator is connected to a regenerated catalyst lift pipe, the catalyst outlet of the first reactor gas-solid separator is located at the bottom of the reaction zone, the gas outlet of the first reactor gas-solid separator is located in the settling zone, the inlet of the second reactor gas-solid separator is located in the settling zone, the catalyst outlet of the second reactor gas-solid separator is placed in the reaction zone, the gas outlet of the second reactor gas-solid separator is connected to the product gas outlet, and the reactor stripper passes through the reactor shell from outside to inside at the bottom of the turbulent fluidized-bed reactor and is opened in the reaction zone of the turbulent fluidized-bed reactor;

a catalytic cracking lift pipe, the bottom of the catalytic cracking lift pipe is connected to the outlet of a catalytic cracking inclined pipe and is provided with a hydrocarbons with 5 or more carbons inlet, and the outlet of the catalytic cracking lift pipe is connected to the settling zone of the turbulent fluidized-bed reactor; and a fluidized-bed regenerator, the fluidized-bed regenerator comprises a regenerator shell, a regenerator feed distributor, a regenerator gas-solid separator, a regenerator heat extractor, a flue gas outlet and a regenerator stripper, wherein the lower part of the fluidized-bed regenerator is a regeneration zone, the upper part of the fluidized-bed regenerator is a settling zone, the regenerator feed distributor is placed at the bottom of the regeneration zone, the regenerator heat extractor is placed in the regeneration zone, the regenerator gas-solid separator is placed in the settling zone or outside the regenerator shell, the inlet of the regenerator gas-solid separator is disposed in the settling zone, the catalyst outlet of the regenerator gas-solid separator is disposed in the regeneration zone, the gas outlet of the regenerator gas-solid separator is connected to the flue gas outlet, and the regenerator stripper is opened at the bottom of the regenerator shell;

wherein, the bottom of the reactor stripper is provided with a reactor stripping gas inlet, the bottom of the reactor stripper is connected to the inlet of a inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spend catalyst lifting gas inlet, and the outlet of the spent catalyst lift pipe is connected to the settling section of the fluidized-bed regenerator;

the bottom of the regenerator stripper is provided with a regenerator stripping gas inlet, the bottom of the regenerator stripper is connected to the inlet of a inclined regenerated catalyst pipe, a regenerated catalyst sliding valve is arranged in the inclined regenerated catalyst pipe, the outlet of the inclined regenerated catalyst pipe is connected to the inlet of the regenerated catalyst lift pipe, the bottom of the regenerated catalyst lift pipe is provided with a regenerated catalyst lifting gas inlet, and the outlet of the regenerated catalyst lift pipe is connected to the inlet of the first reactor gas-solid separator;

the bottom of the regenerator stripper is further connected to the inlet of the catalytic cracking inclined pipe, and a catalytic cracking sliding valve is arranged in the catalytic cracking inclined pipe;

the first reactor gas-solid separator, the second reactor gas-solid separator and the regenerator gas-solid separator are cyclone separators; and the spent catalyst passes through the reactor stripper, the inclined spent catalyst pipe, the spent catalyst sliding valve and the spent catalyst lift pipe into the settling section of the fluidized-bed regenerator;

a regeneration medium enters the regeneration zone of the fluidized-bed regenerator from the regenerator feed distributor, the regeneration medium reacts with the spent catalyst to perform calcination to produce a flue gas containing CO and $CO_2$ and the regenerated catalyst, and the flue gas is discharged after dust removal by the regenerator gas-solid separator;

a part of the regenerated catalyst passes through the regenerator stripper, the inclined regenerated catalyst pipe, the regenerated catalyst sliding valve and the regenerated catalyst lift pipe into the inlet of the first reactor gas-solid separator, and enters the bottom of the reaction zone of the turbulent fluidized-bed reactor after gas-solid separation; another part of the regenerated catalyst passes through the regenerator stripper, the catalytic cracking inclined pipe and the catalytic cracking sliding valve into the catalytic cracking lift pipe;

a reactor stripping gas enters the reactor stripper via the reactor stripping gas inlet and contacts countercurrent with the spent catalyst, and then enters the turbulent fluidized-bed reactor; a spend catalyst lifting gas enters the spent catalyst lift pipe via the spend catalyst lifting gas inlet and contacts cocurrent with the spent catalyst, and then enters the settling section of the fluidized-bed regenerator;

a regenerator stripping gas enters the regenerator stripper via the regenerator stripping gas inlet and contacts countercurrent with the regenerated catalyst, and then enters the fluidized-bed regenerator; a regenerated catalyst lifting gas enters the regenerated catalyst lift pipe via the regenerated catalyst lifting gas inlet and contacts cocurrent with the regenerated catalyst, and then enters the inlet of the first reactor gas-solid separator.

* * * * *